United States Patent [19]

Applegate

[11] 4,088,130
[45] May 9, 1978

[54] HINGE FOR KNEE BRACE

[75] Inventor: Leslie T. Applegate, Cincinnati, Ohio

[73] Assignee: Surgical Appliance Industries, Inc., Cincinnati, Ohio

[21] Appl. No.: 797,120

[22] Filed: May 16, 1977

[51] Int. Cl.² .............................................. A61F 3/00
[52] U.S. Cl. ........................................ 128/80 F; 3/22
[58] Field of Search ................ 128/80 R, 80 F, 80 C, 128/88; 3/22

[56] References Cited

U.S. PATENT DOCUMENTS

| 911,243 | 2/1909 | Johannesen | 128/80 F |
| 2,410,560 | 11/1946 | Witte | 128/80 F X |
| 2,578,108 | 12/1951 | Thornton | 128/80 F |

FOREIGN PATENT DOCUMENTS 490,121  2/1954  Italy ............................................. 3/22

Primary Examiner—John D. Yasko
Attorney, Agent, or Firm—Wood, Herron & Evans

[57] ABSTRACT

A hinge for a knee brace including upper and lower pivotally connected hinge elements. The upper hinge element is provided with inner and outer arcuate notches centered at different radii from the hinge pivot point. The slots cooperate with a stationary pin and a selectively positionable moveable pin on the lower hinge element. Depending on the position of the moveable pin, the hinge elements are either locked at an angle of 180° or their angulation limited to pivotal movement within a preselected variable range, such as, 135°–180°, 90°–180°, 45°–180°, etc.

4 Claims, 7 Drawing Figures

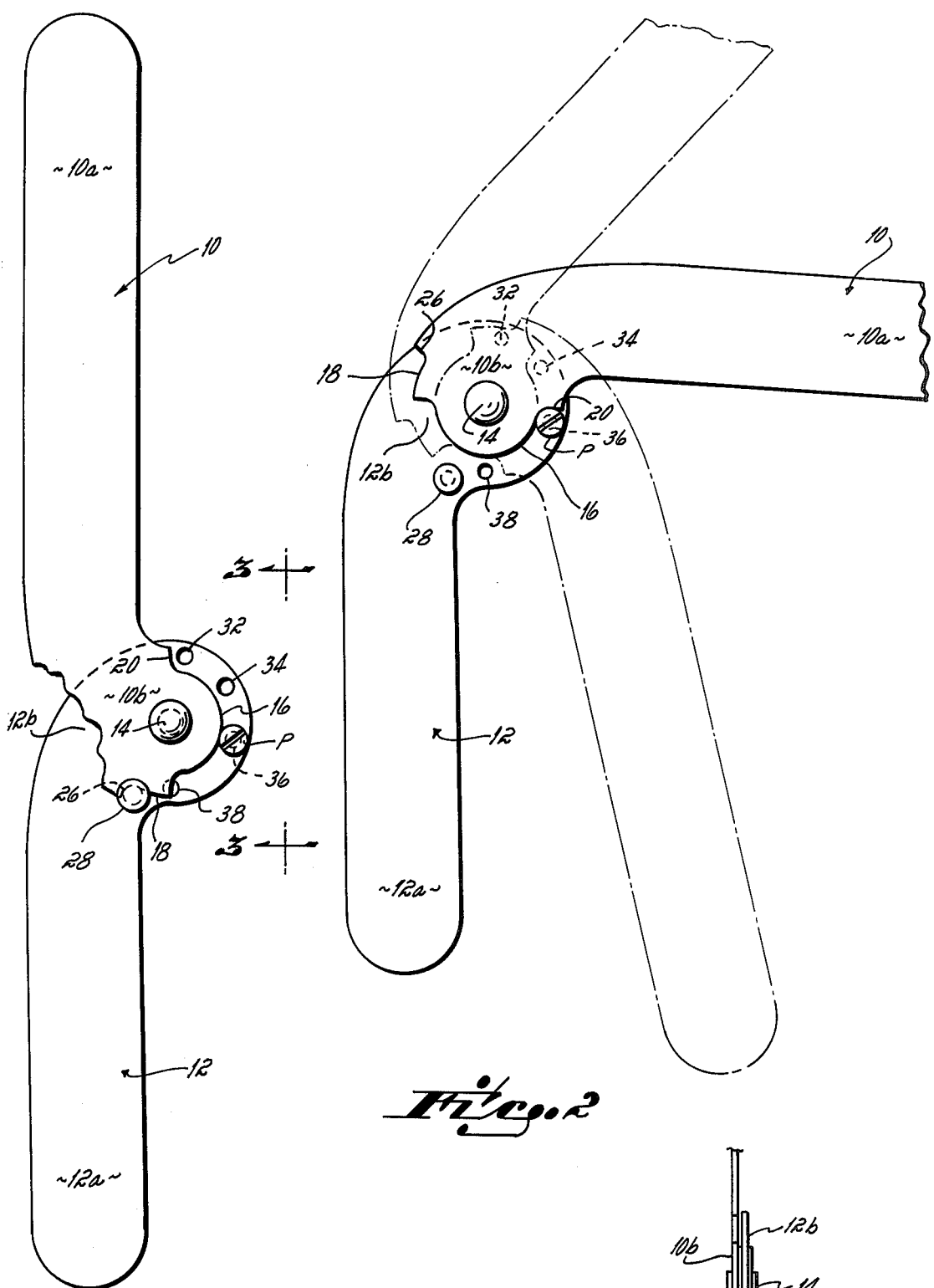
Fig. 1
Fig. 2
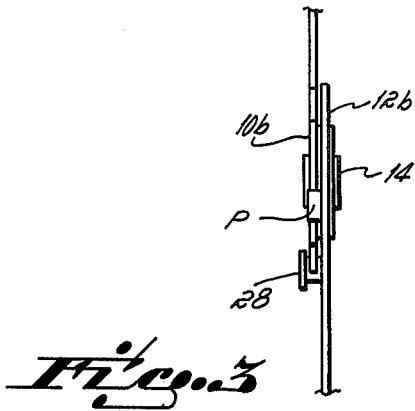
Fig. 3

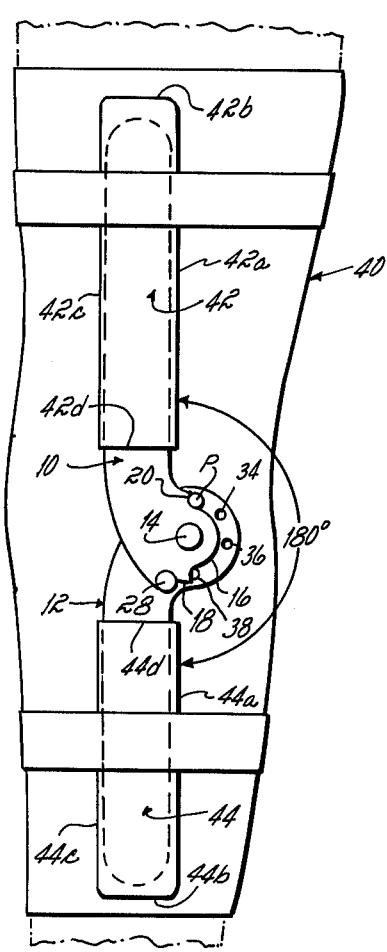
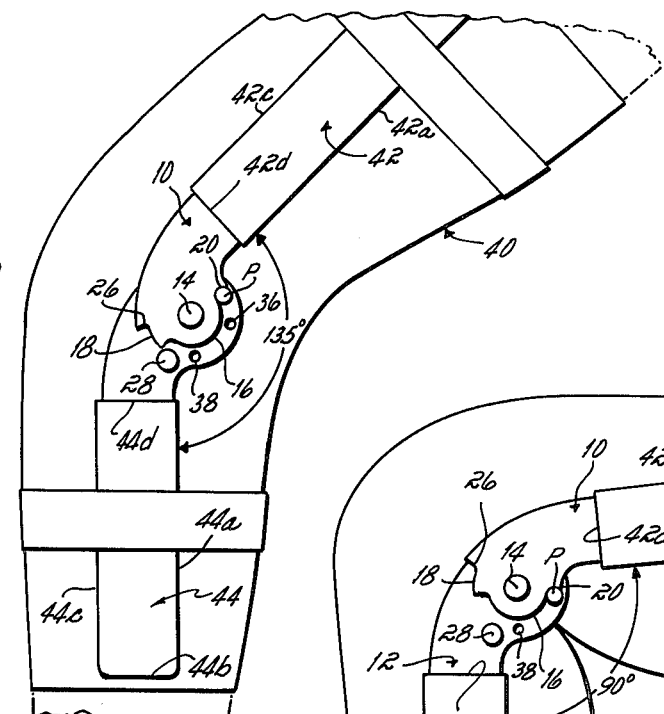
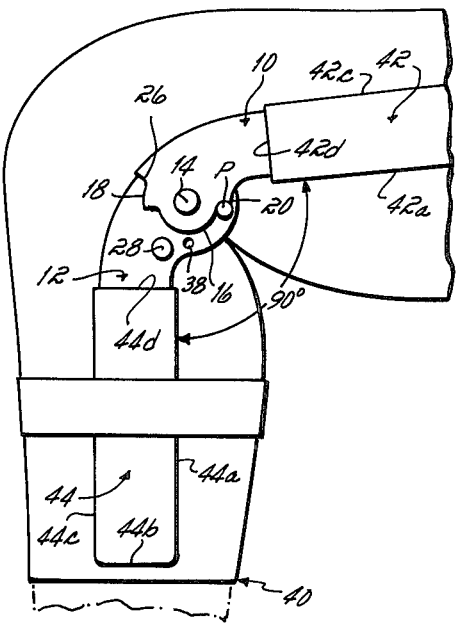
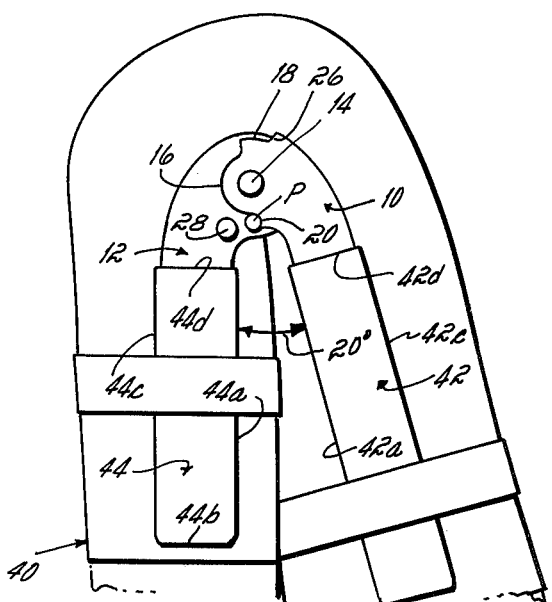

HINGE FOR KNEE BRACE

This invention relates to hinge assemblies, and more particularly to a hinge for use in conjunction with a knee brace for variably selectively restricting bending of the knee.

Knee braces of the type with which the hinge of this invention is useful typically include an elastic sleeve. Mounted to the sleeve on opposite sides thereof are separate hinges. Such hinged knee braces have been proven to be of very considerable utility in stabilizing the wearer's knee. In certain cases, it is desirable that the knee brace user either not be permitted to bend his knee at all, or if permitted to bend his knee, that the bending motion be limited to some preselected angular range, such as, between a fully straightened position (180°) and a partially bent position (e.g., 135°, 90°, 45°). Ideally, a knee brace hinge of the type noted should be easy to use, i.e., simple to adjust, as well as be reliable, lightweight, and inexpensive. In addition, it should not have an undue number of removable parts which can become lost in use. Finally, it should be relatively streamlined in shape with a minimum of projecting parts, sharp corners, or the like which can snag or tear clothing or provide a source of discomfort to the wearer.

It has been an objective of this invention to provide a knee brace hinge having the foregoing characteristics. The objective has been accomplished, in accordance with the principles of this invention, by providing a hinge having upper and lower elongated pivotally connected hinge elements. On one of the hinge elements inner and outer arcuate notches located at different radii from the pivot point, terminating in shoulders or abutments are provided. A single fixed stop or pin on the other unslotted hinge element cooperates with a shoulder defined by one of the notches to preclude hinge movement beyond an angle of 180° corresponding to a fully straightened leg. A single removable pin receivable in one of an associated plurality of pin-receiving apertures also located in the unslotted hinge element cooperates with a shoulder defined by the other notch to either lock the hinge elements at 180° or limit bending thereof to a selected one of a plurality of preset minimum angles such as 135°, 90° or 45° depending upon the particular aperture the removable pin is placed in.

With the hinge of this invention only a single removable pin selectively cooperating with a pair of apertures is necessary to either selectively lock the hinge elements at approximately 180° or limit angulation thereof to no less than a predetermined lesser angle. Stated differently, and assuming three apertures are provided, with this invention only a fixed and removable pin are needed to selectively either lock the hinge elements at approximately 180° or limit angulation to no less than a selected one of two different predetermined lesser angles.

These and other advantages, features and objectives of the invention will become more readily apparent from a detailed description thereof taken in conjunction with drawings in which:

FIG. 1 is a side elevational view of the hinge of this invention partially cut-away, showing the upper and lower hinge elements angulated at approximately 180°, FIG. 2 is a side elevational view of the hinge showing the upper hinge element at varying angular positions with respect to the lower hinge element, FIG. 3 is a front elevational view of the hinge in the region of the hinge pivot, as viewed generally at line 3—3 of FIG. 1, and FIGS. 4, 5, 6 and 7 are side elevational views of a knee brace incorporating the hinge of this invention, showing the hinge elements in varying angulated positions ranging from 180° to approximately 45°, which accompany leg movement from a fully straightened position to a position of maximum bending.

The hinge of this invention includes an upper hinge element 10 and a lower hinge element 12. The upper hinge element 10 includes an upper elongated arm 10a and a lower section 10b of generally flat configuration. The lower hinge element 12 includes a lower elongated arm 12a and an upper section 12b of generally flat configuration. Preferably, the upper hinge element 10 and the lower hinge element 12 are fabricated of stiff steel band stock. The lower section 10b of upper hinge element 10 and the upper section 12b of lower hinge element 12 are in face-to-face superimposed overlapping relation and pivotally connected by a pin 14 having its axis disposed perpendicularly to the flat planar surfaces of the overlapping hinge sections 10b and 12b. With the upper and lower hinge arms 10a and 10b so connected by pin 14, the hinge elements 10 and 12 pivot about an axis passing through the pin 14 perpendicular to the faces of overlapping sections 10b and 12b.

One of the upper or lower hinge elements 10 or 12, for example, the upper hinge element 10, is provided with a first, or inner, arcuate notch 16 which includes a first, or inner, circular arc segment centered about the pin 14. The upper hinge element 10 also includes a second, or outer, arcuate notch 18 which includes a second, or outer, circular arc segment centered about the pin 14 at a radius different from that of the inner notch 16. The inner notch 16 defines a first shoulder 20. The outer notch 18 defines a second shoulder 26.

The upper section 12b of the lower hinge element 12 is provided with a limit stop in the form of a pin 28 disposed perpendicularly to the plane of the surface 12b. The pin 28 is permanently anchored in a suitable aperture formed in the upper section of the lower hinge element. The limit stop or pin 28 is located such that when the upper and lower arms 10a and 12a are angled at approximately 180° to each other, the shoulder 26 in outer notch 18 abut the pin 28 to preclude angulation of the upper and lower hinge elements 10 and 12 beyond approximately 180°, corresponding to a fully straightened leg. The pin 28, when the upper arm is pivoted relative to the lower arm, travels in a path coincident with the outer notch 18.

The upper section 12b of the lower arm 12 is also provided with a pin-receiving aperture 32. The aperture 32 is located relative to the shoulder 20 of the inner notch 16 such that when the upper and lower hinge arms 10a and 12a are disposed as shown in FIG. 1 at an angle of approximately 180°, a selectively removable pin P engaged in aperture 32 will abut the shoulder 20. The combination of pin P in aperture 32 abutting shoulder 20, and limit stop 28 abutting shoulder 26, cooperate to lock the upper and lower hinge elements at an angulation of approximately 180°, corresponding to a straightened leg.

Also included in the upper section 12b of the lower hinge element 12 is at least one additional pin receiving aperture 34, and preferably a second additional pin receiving aperture 36. Apertures 34 and 36 are located at a distance from the pin 14 corresponding to the radius of the inner notch 16. When the selectively removable pin P is placed in one or the other of the apertures 34 and 36 the minimum angulation of the upper and lower hinge elements is limited to predetermined different angles substantially less than 180°. For example, with the pin P in aperture 34, the hinge arms 10 and 12 cannot be positioned in an angle less than approximately 135° corresponding to a partially bent leg. With the pin P in aperture 36 the upper and lower hinge arms 10 and 12 cannot be placed at an angle less than approximately 90° corresponding to a leg bent at 90°. If desired, a further pin-receiving aperture 38 can be provided at a radial distance from the pin 14 corresponding to that of apertures 32, 34 and 36. With the pin P placed in aperture 38 the hinge elements 10 and 12 can be angled with respect to each other no less than approximately 20° corresponding to a leg positioned at its maximum condition of bending without injury to the knee.

An advantage of the hinge element of this invention is that only a shoulder and a single cooperating removable pin P, which selectively seats in one of at least a pair of apertures, namely, aperture 32 and at least one other aperture 34, 36 or 38, in conjunction with a fixed limit stop and shoulder, is utilized to selectively either lock the hinge elements 10 and 12 at approximately 180° or limit angulation to no less than a predetermined lesser angle. Stated differently, and assuming there are at least three apertures into which pin P can be located, with the hinge assembly of this invention only a fixed and removable pin and two cooperating shoulders are needed to selectively either lock the hinge elements at approximately 180° or limit angulation to no less than two different perdetermined lesser angles.

With reference to FIGS. 4, 5, 6 and 7, the hinge of this invention is shown utilized in connection with a knee-encircling sleeve 40. Sleeve 40 is preferably fabricated of material which is elastic in only a horizontal, circumferential or leg-encircling direction. On each side of the sleeve 40 a pair of inelastic upper and lower pockets 42 and 44 are provided, only one pair of which is shown in FIG. 4. The pockets 42 and 44, in a preferred form, are each constituted by a strip of leather which is stitched along three sides, e.g., sides 42a, 42b and 42c, and 44a, 44b and 44c. Sides 42d and 44d are left unstitched to facilitate insertion of the hinge elements 10a and 12b in the pockets defined by the confronting surfaces of the leather strips 42 and 44 and the respective underlying portion of the elastic sleeve 40.

In FIG. 4, the removable pin P is shown engaged in aperture 32. As such, the upper and lower hinge elements 10a and 12a are locked at an angle of approximately 180° by engagement of pin P against shoulder 20 and pin 28 against shoulder 26. With the hinge elements 10a and 12a so locked, the wearer's knee, which is positioned within sleeve 40 with its bending axis coincident with the axis of the pin 14, is maintained in a straightened position. If it is desired to limit motion of the wearer's knee to a variable position between the fully straightened position shown in FIG. 4 and an angulation of approximately 135°, as shown in FIG. 5, the removable pin P is placed in aperture 34. When pin P is so positioned, any attempt to bend the leg to an angle of less than 135° will be prevented by abutment of pin P against shoulder 20. Of course, the wearer's leg is precluded from extending beyond a straight, or 180°, position by pin 28 which should such bending be attempted, will abut shoulder 26. Similarly, should it be desired to increase the allowable bending range from 180° (FIG. 4) to 90° or 20°, the pin P is engaged in aperture 36 or 38, respectively, as shown in FIGS. 6 and 7, respectively. Of course, should it be desired to restrict angulation of the leg only in the one direction, that is, to preclude straightening the leg beyond a 180° position shown in FIG. 4, the pin P can be altogether removed.

I claim:

1. A knee-stabilizing hinge for a tubular knee-encircling sleeve having upper and lower hinge-receiving pockets disposed on each side of said sleeve, said hinge comprising:

an upper hinge element having an upper elongaged arm receivable in an upper pocket of a knee-encircling sleeve and a lower section of generally flat configuration, a lower hinge element having a lower elongated arm receivable in a lower pocket of said knee-encircling sleeve disposed below and on the same side of the knee as said upper pocket, said lower hinge element having an upper section of generally flat configuration, a pivotal connector interconnecting said upper and lower hinge elements with their respective flat sections in face-to-face superimposed overlapping relation for pivotal movement about an axis perpendicular to the respective planes of said face-to-face superimposed overlapping hinge sections, one of said upper or lower hinge element sections having a first arcuate notch, including a first circular arc segment centered on said axis, said first notch defining at least a first shoulder, said one of said upper or lower hinge element sections having a second arcuate notch, including a second circular arc segment centered on said axis at a distance therefrom different from that of said first notch, said second notch defining at least a second shoulder, a pin permanently secured to said section of the other of said upper or lower hinge elements at a point to abut said second shoulder when said first and second hinge elements form an approximate angle of 180° to preclude angulation of said hinge elements beyond approximately 180°, a selectively removable pin, a first aperture disposed in said section of said other hinge element at a point proximate said first shoulder when said first and second hinge elements form an approximate angle of 180° to facilitate, in conjunction with said permanent pin and second shoulder, locking said hinge elements at an angle of approximately 180° when said selectively removable pin engages said first aperture in abutting relation to said first shoulder, at least one additional aperture in said section of said other hinge element at a point intermediate said permanent pin and first aperture for receiving said removable pin to abut said first shoulder when said hinge elements are angulated to form a predetermined angle substantially less than 180° thereby precluding angulation of said hinge elements to an angle less than said predetermined angle, whereby only a permanent pin and associated shoulder and a removable pin cooperating with two apertures are needed to selectively either lock said hinge elements at approximately 180° or limit angulation to a predetermined lesser angle.

2. The hinge of claim 1 wherein there are at least two additional apertures in said section of said other hinge element at different points intermediate said permanent pin and first aperture for selectively receiving said removable pin to abut said first shoulder when said hinge elements are angulated to form two different predetermined angles each substantially less than 180° thereby selectively precluding angulation of said hinge elements to one or the other of said two predetermined lesser different angles, whereby only a permanent pin and associated shoulder and a removable pin cooperating with three apertures are needed to selectively either lock said hinge element at approximately 180° or limit angulation to one or the other of two predetermined different lesser angles.

3. A knee-stabilizing hinge for a tubular knee-encircling sleeve having upper and lower hinge-receiving pockets disposed on each side of said sleeve, said hinge comprising:

an upper hinge element having an upper elongated arm receivable in an upper pocket of a knee-encircling sleeve and a lower section of generally flat configuration, a lower hinge element having a lower elongated arm receivable in a lower pocket of said knee-encircling sleeve disposed below and on the same side of the knee as said upper pocket, said lower hinge element having an upper section of generally flat configuration, a pivotal connector interconnecting said upper and lower hinge elements with their respective flat sections in face-to-face superimposed overlapping relation for a pivotal movement about an axis perpendicular to the respective planes of said face-to-face superimposed overlapping hinge sections, one of said upper or lower hinge element sections having a first arcuate notch, including a first circular arc segment centered on said axis, said first notch defining at least a first shoulder, said one of said upper or lower hinge element sections having a second arcuate notch, including a second circular arc segment centered on said axis at a distance therefrom different from that of said first notch, said second notch defining at least a second shoulder, a limit stop fixed relative to said section of the other hinge element at a distance from said axis equal to that of said second arcuate segment, said limit stop being located to abut said second shoulder when said first and second hinge elements form an angle of approximately 180°, a selectively removable pin, a pair of spaced apertures selectively removably receiving said pin, said pair of apertures being located in said section of said other hinge element at a distance from said axis equal to that of said first arcuate segment, one of said pair of apertures being located at a point proximate said first shoulder when said first and second hinge elements form an approximate 180° angle to facilitate, in conjunction with said limit stop and second shoulder, locking said hinge elements at an approximate 180° angle when said pin is engaged in said one aperture in abutting relation to said first shoulder, the other of said pair of apertures being located intermediate said limit stop and one aperture for movement in a path aligned with said first notch for receiving said removable pin to abut said first shoulder when said hinge elements are angulated to form a first predetermined angle substantially less than 180° thereby precluding angulation of said hinge elements to an angle less than said predetermined angle, whereby only a single removable pin and associated first shoulder selectively cooperating with a pair of apertures, in conjunction with a limit stop and second shoulder, are utilized to selectively either lock said hinge elements at approximately 180° or limit angulation thereof to no less than said first predetermined angle.

4. The hinge of claim 3 further including an additional aperture in said section of said other hinge element at a point intermediate said pair of apertures for selectively receiving said removable pin to abut said first shoulder when said hinge elements are at an angle between 180° and said predetermined angle, thereby selectively precluding angulation of said hinge elements to a second predetermined angle between 180° and said first predetermined angle, whereby only a single removable pin and associated first shoulder selectively cooperating with the three apertures in conjunction with a limit stop and second shoulder, are utilized to selectively either lock said hinge elements at approximately 180° or limit angulation thereof to no less than said first or second predetermined angle.

* * * * *

UNITED STATES PATENT AND TRADEMARK OFFICE
CERTIFICATE OF CORRECTION

PATENT NO. : 4,088,130
DATED : May 9, 1978
INVENTOR(S) : Leslie T. Applegate

It is certified that error appears in the above-identified patent and that said Letters Patent are hereby corrected as shown below:

Col. 3 Line 36 "perdetermined" should be --predetermined--

In the claims:

Col. 4 Line 15 "elongaged" should be --elongated--

Signed and Sealed this

Twenty-fourth Day of October 1978

[SEAL]

Attest:

RUTH C. MASON
Attesting Officer

DONALD W. BANNER
Commissioner of Patents and Trademarks